United States Patent [19]

Sargeant

[11] Patent Number: 4,887,474
[45] Date of Patent: Dec. 19, 1989

[54] CLAMP TIGHTNESS TOOL FOR STATOR CORES

[75] Inventor: John B. Sargeant, Oviedo, Fla.

[73] Assignee: Westinghouse Electric Corp., Pittsburgh, Pa.

[21] Appl. No.: 306,187

[22] Filed: Feb. 6, 1989

[51] Int. Cl.[4] .............................................. G01N 3/08
[52] U.S. Cl. ..................................... 73/865.9; 73/832
[58] Field of Search ................. 73/760, 818, 826, 831, 73/832, 865.3, 865.9

[56] References Cited

U.S. PATENT DOCUMENTS

| | | | |
|---|---|---|---|
| 3,639,987 | 2/1972 | Page | 73/832 |
| 3,943,755 | 3/1976 | Arii et al. | 73/597 |
| 4,368,657 | 1/1987 | Buschmann et al. | 73/159 |

OTHER PUBLICATIONS

"Technology of Heavy Electric Machine Building", Hydrogenators -Zundelevich & Prutkovskii.

*Primary Examiner*—Robert R. Raevis

[57] ABSTRACT

A clamp tightness gauge determines the tightness of compressed sections having passages extending between the adjacent sections. The gauge has a frame to which a pair of spaced apart fingers are attached. The fingers have insertable opposed ends adapted to be inserted in a passage extending between adjacent sections. At least one (and preferably both) of the insertable ends is resilient. A wedge member is attached to an arm pivotably attached to the frame and has a tapered end slideably engaged with the insertable ends of the fingers for urging the fingers against the adjacent sections. The pivotable arm is in operative engagement with an externally threaded member moveably mounted on the frame. An indicator is connected to the wedge member for determining the displacement of its tapered end. Another indicator is connected to the pivotable arm for determining the forces exerted on the tapered end of the wedge member by the adjacent sections. Advancing the threaded member against the resilient arm of the pivotable arm causes the tapered end of the member to penetrate into the spaced between the insertable ends of the fingers and the tapered end of the wedge member to urge the fingers against the sections.

11 Claims, 2 Drawing Sheets

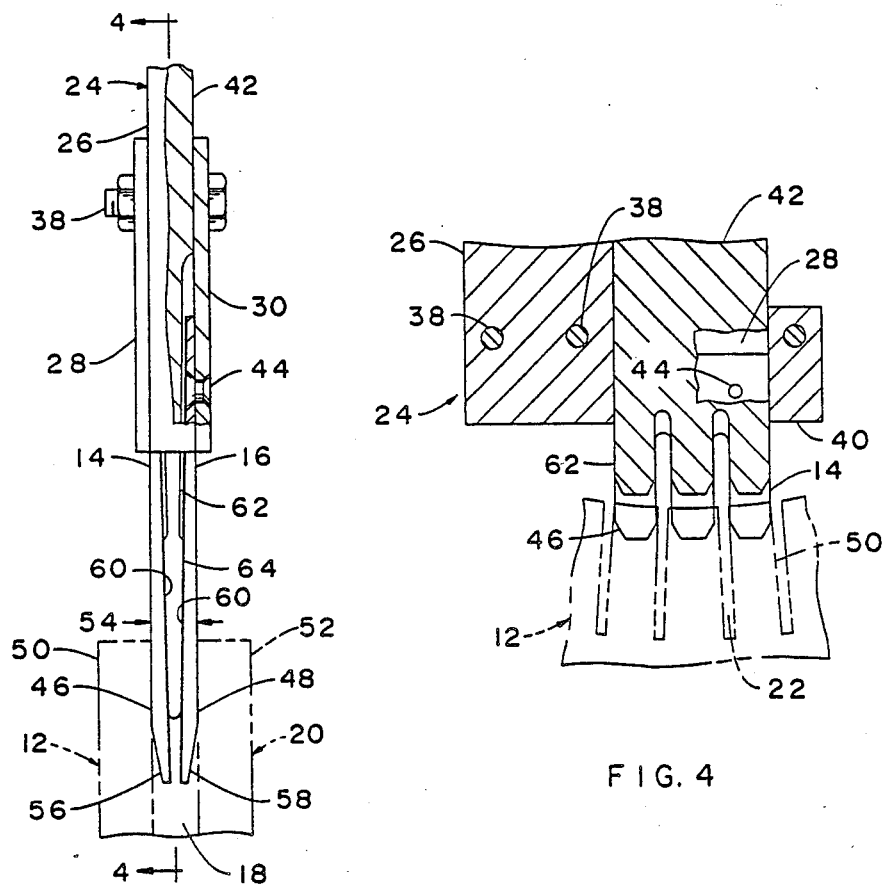
FIG. 3
FIG. 4
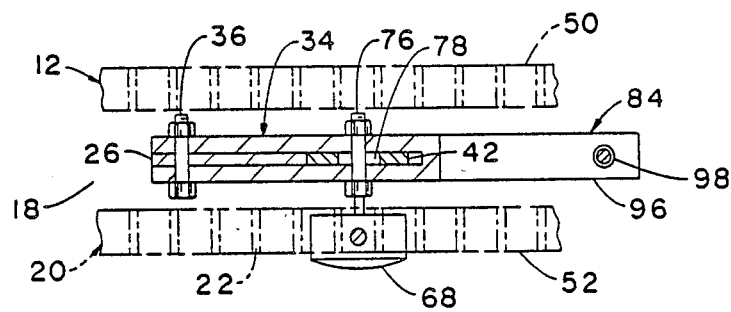
FIG. 5

CLAMP TIGHTNESS TOOL FOR STATOR CORES

This invention relates to a clamp tightness tool. It is particularly useful for determining the clamping tightness of compressed sections having passages between adjacent sections, such as the stator core sections of electric generators.

BACKGROUND OF THE INVENTION

Stator cores of electric generators generally have stator windings looped through axially aligned slots in axially adjacent sections of laminations or punchings of electrical steel with radially extending ventilation slots between adjacent core sections for circulating a coolant gas through the stator. The stator cores are generally assembled by pressing core sections together between two core support plates, tensioning several through-bolts extending between the core support plates to tightly clamp the stator core sections and then looping the windings through the axially aligned slots in the core sections. The clamping tightness is checked and rechecked many times during each step of the assembly process and the through bolts are repeatedly tightened, loosened and then retightened. If the core sections are not tightly clamped in the stator, the core sections will vibrate when the generator is operating, which will result in electrical noise and possible physical damage to the insulative coatings on the steel sheets. The sheets may also be subject to contact corrosion. If the sections are clamped together too tightly, the lacquer films applied to stator core sections may be crushed.

As discussed by M. I. Zundelevich and S.A. Prutkovskii in their work "Technology of Heavy Electric Machine Building - Hydrogenerators", clamping tightness is routinely determined by a knife test. In such a test, a shop floor worker manually inserts a tapered side of a knife into a ventilation passage extending between adjacent stator core sections. Zundelevich et al. illustrates a knife having a tapered face about 40 millimeters long which is inserted into a passage up to a depth of about 2 millimeters. The worker then makes a judgment whether the core sections are properly tightened based upon the felt resistance to the penetration of the knife. Thus the test itself is highly subjective and not infrequently results in unnecessary repetitions of the assembly substeps. In addition, the knife test is effected by the condition of the surface of the core sections and the frictional resistance presented to the knife in addition to clamping tightness. Furthermore, the knife may damage the laminations of the adjacent core sections if the knife is not carefully inserted.

Zundelevich et al. describe a pneumatic knife which improves the reliability of knife tests. In the described test, an air cylinder at a predetermined pressure operates a plunger which urges the edge of a knife against an adjacent core section. The worker then merely reads a scale indicating the plunger travel to determine clamping tightness. Although more reliable readings are consistently made with such a pneumatic knife, the test may still be affected by the surface condition of the lamination adjacent the edge of the knife.

It is therefore an object of the present invention to provide a gauge for more reliably determining the clamping tightness of compressed sections.

It is a further object of the invention to provide a clamping tightness gauge which determines the tightness of stator core sections independently of the condition of their surfaces.

SUMMARY OF THE INVENTION

With these objects in view the present invention resides in a gauge for determining the clamping tightness of compressed sections such as stator core sections having passages between adjacent core sections. The gauge generally has a pair of spaced apart fingers attached to a frame and opposed insertable ends adapted to be inserted into a passage between adjacent sections. At least one, and preferably both, of the insertable ends are made of a resilient material. An arm is pivotably attached to the frame with a loading means moveably mounted on the frame in operative engagement with the arm for pivoting the arm. A wedge member is attached to the pivotably attached arm and has a tapered end slideably engaging the opposed insertable ends of the fingers for urging the opposed insertable ends of the fingers against the adjacent sections when the loading means operatively engages the pivotably attached arm. The gauge has a means for determining the slideable displacement of the tapered ends of the wedge member and a means for determining the force exerted on the tapered end of the wedge member by the adjacent stator core sections through the insertable ends of the fingers for determining the tightness of the sections. In a preferred embodiment of the tool, the tapered end of the wedge member slides on a TEFLON coated surface or other coating which provides a smooth surface with low frictional resistance.

DESCRIPTION OF THE DRAWINGS

The invention will becomes more readily apparent from the following description of a preferred embodiment thereof shown, by way of example only, in the accompanying drawings, wherein:

FIG. 3 is an enlarged end view of the fingers and the tapered end of the wedge member shown in FIG. 2 as generally indicated by arrow 3;

FIG. 4 is a partly fragmentary front sectional view of the fingers and the tapered end of the wedge member shown in FIG. 3 taken along section line 4—4; and FIG. 5 is a plan sectional view of the pivotable arm shown in FIG. 1, taken along section line 5—5.

DETAILED DESCRIPTION

Figure 1:
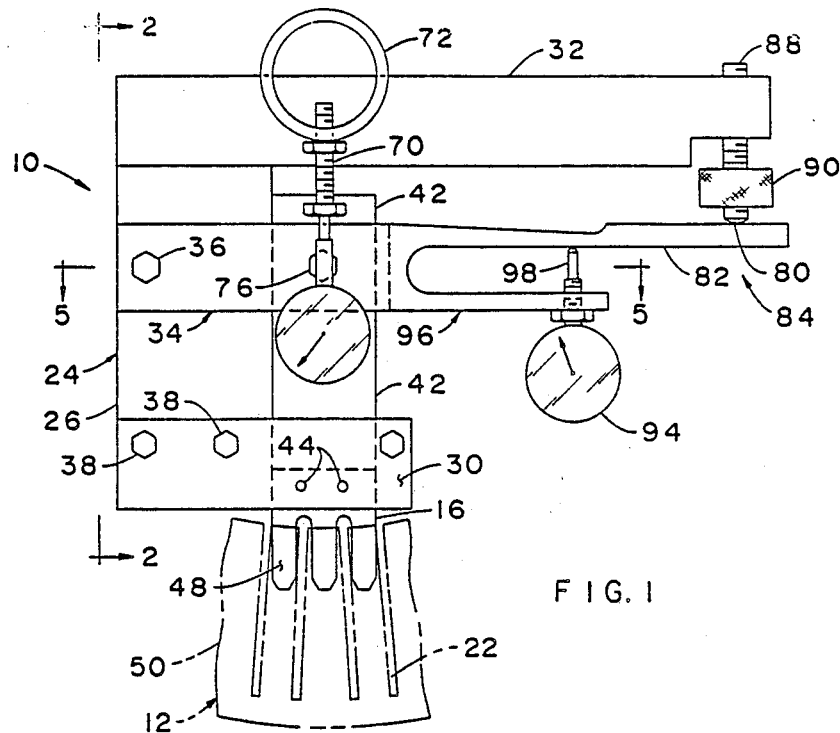
FIG. 1 is a front view of a gauge embodying the present invention with its fingers inserted in a passage axially adjacent a stator core section partially shown in phantom behind the fingers.
Figure 2:
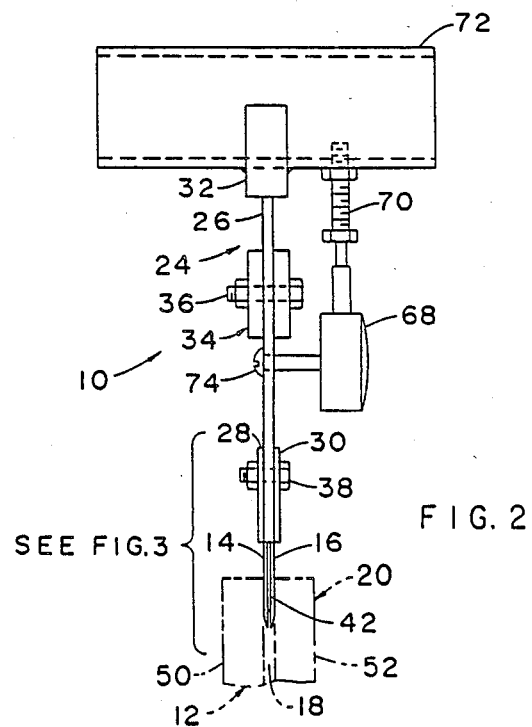
FIG. 2 is an end view of the gauge shown in FIG. 1, taken along line 2—2.

FIG. 1 generally shows a clamp tightness gauge 10 embodying the present invention as it would be employed to determine the clamping tightness of a stator core comprising a stator core section 12 and an axially adjacent stator core section 20 (shown in FIGS. 2 and 3). Thus, the gauge has a pair of spaced apart fingers 14,16 inserted into a passage 18 extending between the stator core sections 12,20. The passage 18 shown is a ventilation groove, typically one-eighth to one-quarter of an inch wide, conventionally built into core vent slots. Conductor windings (not shown) are looped through axially extending slots 22 in completely assembled stator cores.

The clamp tightness gauge 10 generally has a frame 24 which includes a holder member 26 fixedly supporting a pair of opposed spaced apart keepers 28, 30 and a mounting arm 32. A pivotable arm 34 is attached to the holder member 26 by a bolt 36 or other suitable pivoting means.

The keeper 28, 30 are attached to the holder member 26 by a pair of bolts 38. A filler member 40 is fastened between the ends of the keepers 28, 30 to maintain the keepers 28, 30 in spaced relationship and to provide a guide for a wedge member 42 which slideably engages the fingers 14, 16.

The keepers 28, 30 support the fingers 14, 16 in spaced apart relation. Thus the fingers 14, 16 may be attached to the keepers 28, 30 by a pair of rivets 44 or other suitable fastening devices. The fingers 14,16 have insertable ends 46, 48, respectively, adapted to be inserted into the passage 18 between the teeth 50, 52 of the axially adjacent stator core sections 12, 20 respectively. Thus the transverse dimension 54 of the fingers 14, 16 is approximately the same as the distance between adjacent teeth 50, 52. Preferably, the fingers 14, 16 also have tapered outer surfaced 56, 58, respectively, for facilitating the initial insertion of their insertable ends 46, 48 into the passage 18. The insertable ends 46, 48 of the fingers 14, 16 are resilient so that they can be urged against the teeth 50, 52 of the stator core sections 12, 20, respectively. If the insertable ends 46,48 are made of steel, or similar materials, they are preferably coated with TEFLON or other smooth coating 60 having a low coefficient of friction. The insertable ends 46, 48 of the fingers 14, 16, respectively, are also tined as shown in FIG. 4 so that they may be inserted between several pairs of opposing teeth in the adjacent stator core sections, such as teeth 50, 52, with the windings axially extending between the inserted tines.

The wedge member 42 is slideably moveable within the space defined by the fingers 14, 16 with its displacement being guided by the edges of the holder member 26 and the filler member 40. As shown in FIGS. 3 and 4, the wedge member 42 has tines 62 with tapered ends 64 slideably engaged with the opposed resilient ends 46, 48 of the fingers 14, 16, respectively. Thus the wedge member 42 is slideably guided along four of its sides. The tapered ends 64 of the tines 62 of the wedge member 42 urge the opposed resilient ends of the fingers 14, 16, respectively, against the teeth 50, 52 of the adjacent stator core sections 12, 20 respectively, as the tines 62 of the wedge member 42 slideably move between the opposed resilient ends 46, 48 in the passage 18. The test is therefore not affected by the condition of the surfaces of the stator core sections 12, 20 because sliding displacement occurs within the fingers 14, 16 and, preferably, on a smooth surface 60.

The penetration of the tapered ends 64 of the tines 62 of the wedge member 42 into the passage 18 may be determined by means of an indicator 68 which senses the displacement of the wedge member 42 relative to the frame 24. The drawings show an indicator 68 which is preferred because it is easy to use, reliable and capable of withstanding a certain amount of physical mishandling. The indicator 68 shown in fixedly mounted via its extensible stem 70 to a tubular member 72 welded to the mounting arm 32 fixed to the holder member 26. The tubular member 72 also serves as a handle for carrying and using the gauge 10. The indicator 68 is connected to the wedge member 42 by a screw 74, as may be seen in FIG. 2. Displacement of the tines 62 of the wedge member 42 between the ends 46, 48 of the fingers 14, 16 is inversely related to the taper of the tine ends 64. Thus, the displacement increases as the taper angle decreases. Preferably a taper is provided which results in a linear movement of about a tenth of an inch (2.5 mm).

The linear movement of the wedge member 42 is controlled by a bolt 76 extending through a slot 78 in the wedge member 42 which is fastened to the pivotable arm 34 (FIG. 5). The slot 78 permits the bolt 76 to slide transversely of the wedge member 42 as the arm 34 pivots about the bolt 36 and the wedge member 42 is linearly guided by the holder member 26 and the filler member 40 disposed between the keepers 28, 30. The pivotable arm 34 has a loading point 80 operatively engaging a loading means for causing the arm 34 to pivot. FIG. 1 shows a loading point 80 disposed on a slender resilient prong 82 (FIG. 1) of a forked end 84 of the pivotable arm. A threaded member 88 having a thumb nut 90 or other convenient manual device threadably engages a threaded bore (not shown) of the mounting arm 32 fixed to the holder member 26 for moving the threaded member 88 along its axis in operative engagement with the resilient prong 82. As the threaded member advances and engages the resilient prong 82 to pivot the arm clockwise in FIG. 1 and thereby cause the tapered end 64 of the wedge member 42 to further penetrate into the passage 18 between the adjacent stator core sections 12, 20, the teeth 50, 52 of the adjacent core sections 12, 20 exert an increasing resistive force in opposition to the load acting on loading point 80 which causes the resilient prong 82 of the pivotably attached arm 34 to bend. The resistive forces acting upon the tapered end 64 of the wedge member 42 through the fingers 14, 16 is due to the clamping tightness of the core. Thus these forces can be determined by measuring the deformation of the resilient prong 82. FIG. 1 and 5 show a preferred indicator 94 mounted on a rigid prong 96 of the forked end 84 of the pivotable arm 34 with a displacement sensing element 98 adjacent the resilient prong 82. As the load and the resistive forces urge the resilient prong 82 against the sensing element 98, the indicator 94 will indicate the extent of deformation of the resilient arm 82 and indirectly the magnitude of the resistive forces.

The clamping tightness may be determined by merely reading the linear movement of the wedge member 42 at a predetermined resistive force (as is done in the pneumatic knife test) or alternatively by reading the resistive force for a predetermined linear movement (as is done in the manual knife test). Preferably, clamping tightness is determined by reading both the linear movement of the wedge member 42 and the resistive force and then comparing a ratio of the two determinations with a known standard.

When the gauge 10 is used, the insertable ends 46, 48 of the fingers 14, 16 are first manually inserted in a passageway 18 up to a point where one of the indicators 68,94 begins to indicate a reading other than zero. The indicator bezels are rotated to indicate zero readings. The thumb nut 90 on the loading means 88 is then rotates to advance the tapered ends 64 of the tines 62 of the wedge member 42 into the passageway 18. When the force reading indicator 94 just moves off zero, the indicators 68, 94 are zeroed (if necessary). The wedge member 42 is then advanced about a tenth of an inch (2.5 mm) and the indicators are read. The thumb nut is then rotated in the opposite direction to relieve the resistive forces acting on the insertable ends 46, 48 of the fingers 14, 16, respectively, and the gauge 10 is withdrawn from the passageway 18.

While a presently preferred embodiment of the invention has been shown and described it is to be distinctly understood that the invention is not limited thereto but may be otherwise variously embodied within the scope of the following claims.

What is claimed is:

1. A clamp tightness gauge for determining the clamping tightness of compressed sections having passages between adjacent section, the gauge having:
   a frame;
   a pair of spaced apart fingers having opposed insertable ends adapted to be inserted into a passage between compressed adjacent sections, at least one insertable and being resilient;
   an arm pivotably attached to the frame;
   a loading means moveably mounted on the frame in operative engagement with the pivotably attached arm for pivoting the arm;
   a wedge member operatively attached to the pivotably attached arm and having a tapered end, the tapered end slideably engaged with the opposed insertable ends of the fingers for urging the opposed insertable ends of the fingers against the sections when the loading means operatively engages the pivotably attached arm;
   means connected to the wedge member for determining the slideable displacement of the tapered end of the wedge member; and
   means connected to the pivotably attached arm for determining the force exerted on the tapered end of the wedge member through the insertable ends of the fingers by the sections.

2. The clamp tightness gauge of claim 1, wherein both of the insertable ends of the fingers are resilient.

3. The clamp tightness gauge of claim 1, wherein each of the insertable ends of the fingers has a coating with a low coefficient of friction against which the wedge member slides.

4. The clamp tightness gauge of claim 1, wherein the insertable opposed ends of the spaced apart fingers have tines adapted to be inserted into the passage.

5. The clamp tightness gauge of claim 4, wherein the tapered end of the wedge member has tines disposed between finger tines and the ends of the wedge tines are tapered.

6. The clamp tightness gauge of claim 1, wherein the slideable wedge member is guided along four of its sides.

7. The clamp tightness tool of claim 1, wherein the arm pivotably attached to the frame has an end operatively engaged with the loading means and the wedge member is attached to the pivotably attached arm between the pivotably attachment and the end in operative engagement with the loading means.

8. The clamp tightness gauge of claim 7, wherein the pivotable arm has a forked end with a resilient prong, the resilient prong being operatively engaged with the loading means.

9. The clamp tightness gauge of claim 8, wherein the forked end of the pivotably attached arm has a rigid prong and the means for determining the force exerted on the tapered end of the wedge member is mounted on the rigid prong with a sensing element adjacent the resilient prong.

10. The clamp tightness gauge of claim 8, wherein the loading means moves the pivotably attached arm parallel to the direction in which the wedge member slides.

11. A clamp tightness gauge for determining the clamping tightness of compressed sections having passages between adjacent sections, the gauge having;
   a frame;
   a pair of spaced apart fingers attached to the frame, the fingers having opposed resilient tined ends adapted to be inserted into a passage between compressed adjacent sections;
   an arm pivotably attached to the frame and having a forked end with a resilient prong and a rigid prong;
   a loading means moveably mounted on the frame in operative engagement with the resilient prong of the forked end of the pivotably attached arm for pivoting the arm;
   a wedge member operatively attached to the pivotably attached arm and having a tapered tined end slideably engaged with the opposed resilient tined ends of the fingers for urging the ends of the fingers against the adjacent sections when the loading means operatively engages the resilient prong of the forked end of the pivotably attached arm;
   means connected to the wedge member for determining the slideable displacement of the tapered end of the wedge member; and
   means having a sensing element, the means connected to the rigid prong of the forked end of the pivotably attached arm with its sensing element adjacent the resilient prong of the forked end of the pivotably attached arm, for determining the force exerted on the tapered tined end of the wedge member through the tined ends of the fingers by the adjacent sections.

* * * * *